United States Patent
Feiweier et al.

(10) Patent No.: US 11,259,752 B2
(45) Date of Patent: Mar. 1, 2022

(54) METHOD FOR ADAPTING A MEDICAL SYSTEM TO PATIENT MOTION DURING MEDICAL EXAMINATION, AND SYSTEM THEREFOR

(71) Applicant: SIEMENS AKTIENGESELLSCHAFT, Munich (DE)

(72) Inventors: Thorsten Feiweier, Poxdorf (DE); Tobias Kober, Lausanne (CH); Gunnar Krueger, Watertown-Boston, MA (US)

(73) Assignee: Siemens Aktiengesellschaft, Munich (DE)

( * ) Notice: Subject to any disclaimer, the term of this patent is extended or adjusted under 35 U.S.C. 154(b) by 274 days.

(21) Appl. No.: 14/665,145

(22) Filed: Mar. 23, 2015

(65) Prior Publication Data
US 2015/0265219 A1    Sep. 24, 2015

(30) Foreign Application Priority Data
Mar. 21, 2014   (EP) ..................................... 14160999

(51) Int. Cl.
*A61B 5/00*  (2006.01)
*G01R 33/565*  (2006.01)
(Continued)

(52) U.S. Cl.
CPC ............ *A61B 5/721* (2013.01); *A61B 5/0033* (2013.01); *A61B 5/74* (2013.01); *A61B 6/527* (2013.01);
(Continued)

(58) Field of Classification Search
CPC ..... A61B 5/0033; A61B 5/0077; A61B 5/024; A61B 5/0402; A61B 5/055; A61B 5/11;
(Continued)

(56) References Cited

U.S. PATENT DOCUMENTS 6,398,731 B1    6/2002 Mumm et al.
8,571,293 B2    10/2013 Ernst et al.
(Continued)

FOREIGN PATENT DOCUMENTS

EP   2428164 A2    3/2012
WO   2004008427 A1    1/2004
WO   2007136745 A2    11/2007

OTHER PUBLICATIONS

Sachs et al., "Real-Time Motion Detection in Spiral MRI Using Navigators", MRM (32), pp. 639-645 (1994) (Year: 1994).*

*Primary Examiner* — James M Kish
(74) *Attorney, Agent, or Firm* — Laurence A. Greenberg; Werner H. Stemer; Ralph E. Locher

(57) ABSTRACT

A method for adapting a medical system to an object movement during medical examination of the object and a medical system configured for carrying out the method. The medical system has a device for detecting and quantifying a motion of the object before or during an acquisition of diagnostic data. The system for detecting and quantifying a motion of the object is able to directly identify and qualify the occurrence of object motion and to automatically suggest an adaptation of the diagnostic data acquisition strategy/technique as a function of the object motion.

14 Claims, 1 Drawing Sheet

(51) Int. Cl.
*A61B 6/00* (2006.01)
*A61B 5/055* (2006.01)
*A61B 5/024* (2006.01)
*A61B 5/113* (2006.01)
*A61B 5/318* (2021.01)

(52) U.S. Cl.
CPC ...... *G01R 33/56509* (2013.01); *A61B 5/0077* (2013.01); *A61B 5/024* (2013.01); *A61B 5/055* (2013.01); *A61B 5/1135* (2013.01); *A61B 5/318* (2021.01); *A61B 5/7285* (2013.01); *A61B 6/46* (2013.01); *A61B 6/541* (2013.01); *A61B 6/545* (2013.01)

(58) Field of Classification Search
CPC ..... A61B 5/1135; A61B 5/721; A61B 5/7285; A61B 5/74; A61B 6/46; A61B 6/527; A61B 6/541; A61B 6/545; A61B 17/3421; A61B 2034/107; A61B 2034/2051; A61B 2034/2053; A61B 2034/2055; A61B 2034/2063; A61B 2090/103; A61B 2090/365; A61B 2090/3735; A61B 2090/3762; A61B 2090/3782; A61B 2090/3983; A61B 5/0555; G01R 33/56509; G01R 33/543; G01R 33/546
See application file for complete search history.

(56) References Cited

U.S. PATENT DOCUMENTS

| | | | |
|---|---|---|---|
| 8,682,112 B2* | 3/2014 | Fukasawa | H04N 5/76 348/439.1 |
| 2004/0092816 A1 | 5/2004 | Ossmann et al. | |
| 2005/0089213 A1* | 4/2005 | Geng | G06K 9/00214 382/154 |
| 2005/0113670 A1 | 5/2005 | Salla et al. | |
| 2006/0052693 A1* | 3/2006 | Tynes | A61B 5/055 600/424 |
| 2007/0083097 A1* | 4/2007 | Fujiwara | A61B 5/0059 600/407 |
| 2007/0088212 A1* | 4/2007 | Takei | A61B 5/055 600/413 |
| 2007/0280508 A1* | 12/2007 | Ernst | A61B 6/0492 382/107 |
| 2008/0123812 A1 | 5/2008 | Sabol et al. | |
| 2008/0309333 A1* | 12/2008 | Stehning | G01R 33/5676 324/307 |
| 2009/0209846 A1* | 8/2009 | Bammer | A61B 5/064 600/421 |
| 2010/0152568 A1* | 6/2010 | Kokubun | A61B 5/055 600/410 |
| 2011/0230755 A1* | 9/2011 | MacFarlane | A61B 5/055 600/414 |
| 2012/0033868 A1* | 2/2012 | Ren | A61B 6/025 382/131 |
| 2014/0140481 A1 | 5/2014 | Yamaguchi | |
| 2014/0163362 A1* | 6/2014 | Pahlevan | A61B 5/021 600/430 |

* cited by examiner

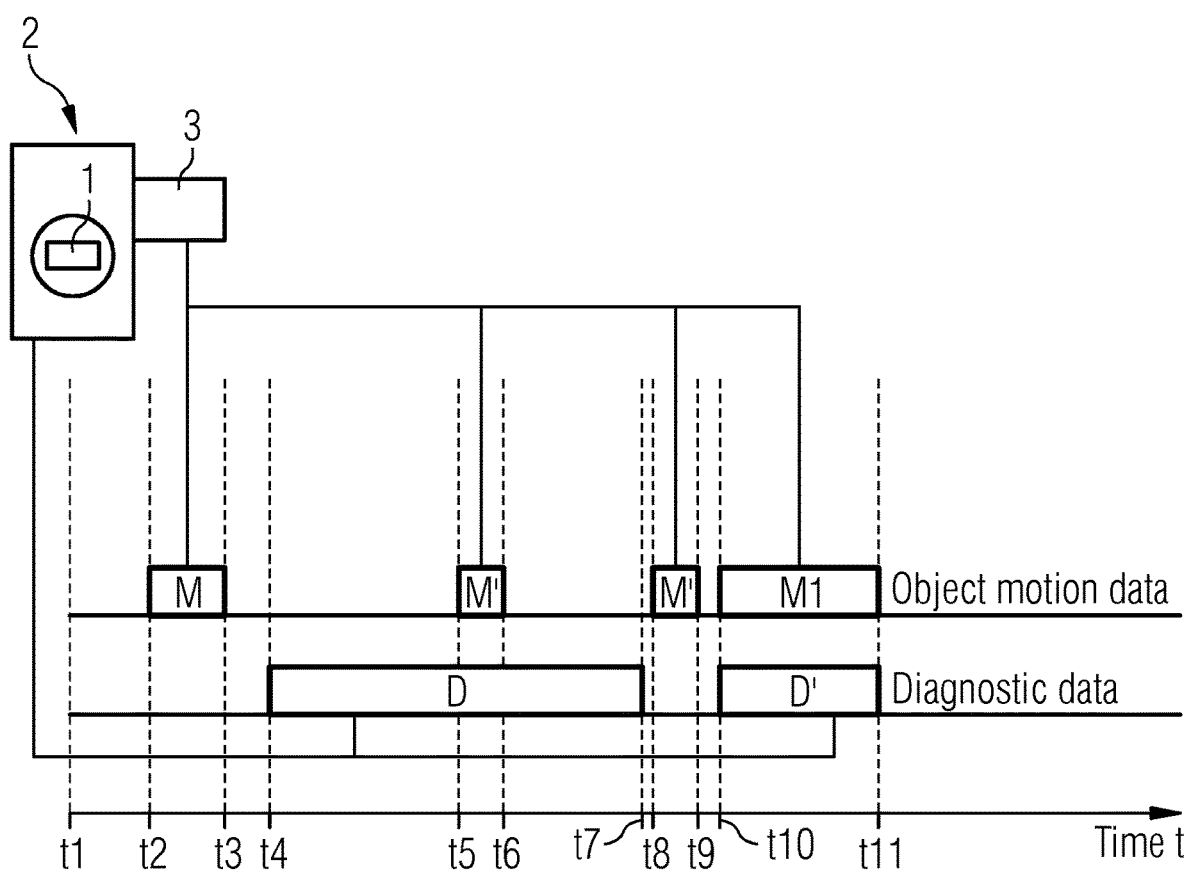

METHOD FOR ADAPTING A MEDICAL SYSTEM TO PATIENT MOTION DURING MEDICAL EXAMINATION, AND SYSTEM THEREFOR

CROSS-REFERENCE TO RELATED APPLICATION

This application claims the priority, under 35 U.S.C. § 119, of European patent application EP 14160999.0, filed Mar. 21, 2014; the prior application is herewith incorporated by reference in its entirety.

BACKGROUND OF THE INVENTION

Field of the Invention

The invention relates generally to medical examination and to patient movements occurring during the medical examination, e.g. in biomedical imaging. More specifically, the invention pertains to a method and a system for optimizing measurement processes in medical systems when undesired patient motion occurs during the medical examination.

When running a medical system, like a Magnetic Resonance Imaging (MRI) sys-tem or a Positron Emission Tomography (PET) system, patient motion occurring during data acquisition has a strong influence on the time needed for acquiring medical data, and thus for making a medical diagnosis. Indeed, the presence of motion during data acquisition may result for instance in image artifacts that can cause major problems in several post-processing procedures and can, in more extreme cases, even affect the diagnostic information. The problem of subject/patient motion during the acquisition of data for medical diagnosis concerns especially children or elderly patients who cannot remain still for the whole duration of the measurement.

Unfortunately, patient motion is often detected too late, for instance in the form of artifacts appearing in the acquired images, and often after processing several measurements or data acquisitions. Notably in medical imaging, patient movements during data acquisition may impact the image quality so that a new data acquisition becomes necessary, sometimes requiring also patient sedation. Patient motion thus increases consequently the time needed for acquiring a medical diagnosis, and of course, the costs of the medical examination.

Different techniques have been proposed to overcome patient motion occurring during data acquisition by means of a medical system. One example is the use of a monitoring camera for observing the patient during data acquisition. The acquisition of data is then stopped by an operator as soon as a motion of the patient is observed, and then, the operator calms or sedates the patient, or manually adapts the strategy of data acquisition in function of the motion. Unfortunately, permanent observation of the patient by the operator is not always possible in a clinical routine, since the operator has often other activities running beside the data acquisition activity (e.g. planning the next data acquisition, processing previously acquired data, etc), and also because the visual field of the monitoring camera might be limited due to the configuration of the data acquisition system (e.g. by the coils of an MRI system) or due to the disposition of the patient himself (e.g. patient under a blanket). Other techniques involve prospective and retrospective motion correction. However, the techniques usually do not cover the complete range of diagnostic applications and typically have limitations regarding the maximum amount of motion they are able to correct.

Consequently, the motion of a patient is typically revealed via the artifacts appearing for example in images. Depending on the medical examination technique, subtle and/or pronounced artifacts might be found, affecting therefore the diagnostic information, e.g. the diagnostic information of an MRI image. If it is determined that patient motion is the source of an artifact, then, an adaptation of the data acquisition strategy might take place. Unfortunately, the setting up of the new strategy can only take place after the detection of the artifacts, i.e. after data have been already acquired and processed. Data corrupted by patient motion have then to be rejected and unfortunately, it might be difficult to determine if artifacts corrupted medical data. For example, the detection of artifacts in already taken MRI images requires an experienced operator capable of making the relation between patient motion and artifact, and might thus also be a source of misinterpretation.

SUMMARY OF THE INVENTION

It is accordingly an object of the invention to provide a method and a system which overcomes the above-mentioned and other disadvantages of the heretofore-known devices and methods of this general type and which provides for early detection and qualifying patient motion in order to adapt the data acquisition strategy/technique of the medical system to the patient motion in an advanced stage for avoiding a loss of time due to the acquisition of motion corrupted data. The method should, moreover, be adapted to clinical routine.

With the foregoing and other objects in view there is provided, in accordance with the invention, a method for adapting a medical system to an object motion occurring during a medical examination of the object by way of the medical system. That is, the objects are achieved according to the present invention with respect to a method for adapting a medical system to an object motion, e.g. of a patient head, occurring during a medical examination of the object by means of the medical system, the medical system working according to a medical technique, e.g. a medical imaging technique of a medical imaging system. The method according to the invention comprises:

placing the object to be examined in an examination volume of the medical system, i.e. in a position and place allowing its examination by the medical system, the examination volume being for example the tube of an MRI scanner;

starting an acquisition of medical data by means of the medical system, wherein the medical data are data representing anatomical or physiological information of the object, the data allowing for example the detection of a medical condition or disease of the object. In particular, medical data might be used for reconstructing a medical image of the object, the medical image being typically used by medical professionals for making a medical diagnosis of the object;

during the acquisition of the medical data:
using object motion data for automatically classifying medical data in two sets of data, respectively a first set of data for which object motion during medical data acquisition is tolerable, and a second set of data for which object motion during medical data acquisition is not tolerable, wherein the object motion data are information related to motion of the object when it is in the examination volume; and rejecting, preferably automatically, medical data belonging to the second set of data and/or adapting, preferentially automatically adapting, the medical data acquisition strategy/technique of the medical system in function of the object motion.

The object according to the invention is in particular a patient or subject to be examined by means of the medical system according to the invention, or part of the patient/subject, such as a head or a joint. Advantageously, the present method does not require any specific repetition of a motion sequence of the object and does not require the acquisition of several repetitions of a same motion: the object is simply placed in the examination volume and relevant motion of the object is detected, wherein relevant motion might be an object motion occurring only once during the medical examination (single occurrence), as well as a repetitive motion, i.e. an object motion occurring several times during the medical examination (multiple occurrence).

The method according to the invention comprises in particular acquiring the object motion data by means of a system for detecting and/or quantifying object motion, wherein the object motion data are acquired when the object is in the examination volume defining the position and place allowing its examination by the medical system. Preferably, the acquisition of object motion data by means of the system for detecting and/or quantifying object motion is performed before starting the acquisition of medical data and/or in parallel to the acquisition of medical data. In particular, if the object motion data are acquired before starting the acquisition of medical data, then the method according to the invention may comprise acquiring during the acquisition of medical data further object motion data for optimizing the classification of medical data in the two sets of data. The method according to the invention preferentially comprises stopping the acquisition of object motion data after a predetermined time period by means of the system for detecting and/or quantifying object motion. Preferably, the method according to the invention comprises calibrating the medical system by means of the object motion data and/or in particular, determining one or several object motion thresholds before starting the acquisition of medical data or in parallel to the acquisition of the medical data.

Preferably, object motion data and medical data are temporarily stored on a storage medium, e.g. a memory, by the system for detecting and/or quantifying object motion and the medical system respectively. Rejecting medical data means in particular erasing the medical data from the storage medium or withdrawing the medical data from medical data processing.

In the case the medical system according to the invention is a medical imaging system, such as for example a Magnetic Resonance Imaging (MRI) system, or a Positron Emission Tomography (PET) system, or a Single-Photon Emission Computed Tomography (SPECT) system, or a Computed Tomography (CT) system, or an X-Ray imaging system, then the present invention allows for example an improvement of the quality of images taken by the medical imaging system working according to a known medical imaging technique. Preferably, each of the medical imaging system according to the invention works according to a medical imaging technique known by the skilled man. The difference between the present invention and the known medical imaging techniques originates in particular in the strategy used for treating the object motion data and adapting the medical data acquisition strategy/technique notably during the medical imaging. Indeed, the present invention proposes a combination of features comprising in particular: the use of a system for detecting and/or quantifying object motion for acquiring object motion data before starting the acquisition of medical data and/or during the acquisition of medical data, when the object is already in an examination volume defining a position and place allowing its imaging/examination by the medical imaging system; the measurement of at least one object motion characteristic from the object motion data; qualifying the object motion for the object motion characteristic (i.e. detecting "relevant" motion of the object) with respect to the imaging procedure used for the medical examination of the object; if relevant motion is detected, then adapting the medical data acquisition strategy/technique by per-forming, preferentially automatically performing, for example at least one of the following actions—which will be described later in more details:

sending a message to an operator, or sending a message to the subject, or preparing a reacquisition, wherein the reacquisition may have to be acknowledged/confirmed by the operator before being preferentially automatically performed by the medical system according to the invention, or preparing a change of the imaging procedure, wherein the change of the imaging procedure may have to be acknowledged/confirmed by the operator before being preferentially automatically performed by the medical system according to the invention, the change of the imaging procedure being for example reducing the scan time (smaller coverage), using imaging procedure with smaller motion sensitivity (by changing the k-space sampling scheme and/or the k-space coverage and/or the MR signal evolution).

Advantageously the object motion data acquired by the system for detecting and/or quantifying object motion are specific to the object and the configuration of the medical (imaging) system.

Methods and systems for detecting and/or quantifying object motion and acquiring object motion data according to the invention are preferentially standard methods known by the skilled man and already used in cooperation with medical system, notably in cooperation with medical imaging. They are for example:

bulk motion detection systems, like cameras, ultrasound sensors, etc.);

pulse measurement system;

breathing belt;

ECG system;

a device for enabling the registration of repeated acquisitions (e.g. time series data)

a device enabling navigator techniques (used e.g. in MRI systems);

a device enabling k-Space-Navigators (for instance for MRI systems);

statistical or other methods evaluating the acquired medical data during the acquisition, permitting to draw conclusions concerning the severity of motion artifacts in the data.

The object motion data and information acquired by means of the above-mentioned methods/systems are used, according to the invention, for adapting, preferentially for automatically adapting, the medical data acquisition strategy/technique in function of the object motion. The adaptation of the medical data acquisition strategy/technique notably refers to:

a change of the acquisition method, e.g. using multi-shot instead of single-shot methods in MRI when "intolerable" motion is detected according to the invention or inversely; and/or changing the measurement parameters, e.g. changing the number of slices acquired to reduce exam duration.

Therefore the claimed adaptation according to the present invention preferentially changes the acquisition method and/or the measurement parameters of the medi-cal system used for acquiring the medical data. In particular, the adaptation per-formed according to the present invention is able to reduce the sensitivity of the medical system to object motion notably by changing the kind of medical data that are acquired or the way they are acquired: for example, in medical imaging, the adaptation may yield to differences in image contrast, resolution, coverage, or definition/sharpness. An example of a change of the acquisition strategy in medical imaging is for instance automatically changing from a scan without prospective motion correction to a scan with prospective motion correction if and only if a certain amount of motion is detected (exceeding the threshold). Preferentially, in the case of medical imaging systems and medical imaging techniques such as MRI, the adaptation according to the present invention comprises:

a change in k-space sampling scheme; and/or
a change in the k-space coverage; and/or
a change in the MR signal evolution; and/or
any combination of the previous changes (1)-(3).

Moreover, the object motion data and information acquired by means of the above-mentioned methods/systems might also be used according to the invention for:

triggering the acquisition of medical data (for example, in the case of periodical motion, like breathing or beating of the heart);

optimizing the image quality by prospective motion correction, e.g. by adapting the coordinate system of the measurement in function of the patient motion;

optimizing the image quality by retrospective motion correction, e.g. by correcting the acquired motion-corrupted data during image reconstruction, notably for MR or PET data acquisition);

reacquisition of data, i.e. acquiring new data for replacing the corrupted data, while no reacquisition is performed for the non-corrupted data.

Advantageously, the method according to the invention allows an early detection of object/patient motion avoiding thus to acquire data that would not be usable for diagnostic images, and leading thus to a decrease of the data acquisition time and cost. Preferentially, the present invention is able to directly identify and qualify the occurrence of object/patient motion and to automatically suggest an adaptation of the medical data acquisition strategy/technique in function of the object/patient/subject motion, and/or to automatically proceed to the adaptation of the medical data acquisition strategy/technique.

Preferentially, the system for detecting and/or quantifying object motion is able to detect object motion and/or to quantify the object motion during the medical data acquisition. Advantageously, the quantification of the object motion comprises in particular a determination of an object motion amplitude and/or direction from the object motion data. For this purpose, a calculator might perform a data treatment analysis of the object motion data in order to quantify the object motion and determine the object motion amplitude from the object motion data. Preferentially, one or several object motion thresholds might be determined and/or pre-defined for the detection of object motion by an operator or in a threshold database of the system for detecting and/or quantifying object motion.

Preferentially, each object motion threshold is specific to the medical technique used for examining the object/subject, e.g. specific to the imaging technique used by the medical imaging system for imaging the object. For example, according to the present invention, a first threshold might be used for a single-shot EPI acquisition and a different threshold is then used for a multi-shot TSE acquisition. In particular, the threshold is automatically selected, e.g. in the threshold database, by the system for detecting and/or quantifying object motion from the medical technique used for examining the object/subject. Preferentially, the selected threshold has to be validated by an operator or its value may be adapted by the operator before being operational for the classification of the object motion data in the two sets of data. In particular, the selection or determination of the threshold by the system for detecting and/or quantifying object motion may take place before starting the acquisition of medical data or in parallel to the acquisition of medical data.

Advantageously, since each medical technique is affected by motion to a different extent (e.g. a sinusoidal nodding of a head with constant frequency and amplitude induces a motion image artifact that looks very different if one considers an image acquired using a single-shot EPI technique or an image acquired using a multi-shot TSE technique: while the EPI image might exhibit a small amount of blurring, the TSE image will show severe ghosting), the present invention proposes an automatic adaptation/selection of the threshold ruling the classification of the object motion data in the two sets of data in function of the medical technique used for examining the object (the threshold defining thus which object motion characteristic, such as amplitude, direction, frequency, etc. is acceptable for the medical technique specifically), wherein the value of the threshold automatically adapted/selected might be tuned by an operator, for instance for increasing or decreasing the threshold value that has been automatically selected by the system for detecting and/or quantifying object motion.

In particular, the thresholds are stored in the threshold database: for example, for a given medical technique, e.g. a given imaging technique such as EPI, TSE, sin-gle/multi-shot, navigated, etc., and a given medical protocol, e.g. a given imaging protocol such as matrix size, FOV, etc., the threshold database provides threshold values that define a maximum tolerable motion characteristic for the object, e.g. a maximum tolerable motion amplitude and/or frequency and/or direction, etc. In function of the medical technique used for examining the object, the system for detecting and/or quantifying object motion is in particular able to automatically choose in the threshold database a threshold value that has been defined for the medical technique. Optionally, the system for detecting and/or quantifying object motion provides the operator with a tuning of the chosen/selected threshold value so that the operator may personally adapt the automatically selected threshold value. Alternatively, the threshold or a maximum artifact level might be directly specified by the operator. In particular, the maximum artifact level, quantified e.g. as the relative intensity of artifacts as compared to the desired image, is calculated/simulated from a MR signal in order to estimate to which motion threshold this would correspond.

Preferentially, object motion data acquired before the examination by means of a medical technique are used for comparing a motion characteristic (e.g. amplitude, direction, frequency) of the object to the threshold defined for the medical technique. Advantageously, the comparison done before starting the acquisition of medical data allows the operator or the medical system according to the invention to decide if the medical examination that will be performed by means of the medical technique will exhibit artifacts beyond the acceptable level. If it is the case, then the medical data acquisition strategy/technique of the medical system is automatically adapted by the medical system according to the invention or might be manually adapted by the operator. In particular, object motion data acquired during the medical examination can be used to check whether the motion characteristics of the object changes during the medical examination. In particular, during the medical examination by means of a medical technique, if a motion characteristic of the object exceeds a threshold recorded in the threshold database for the medical technique, than the medical system and the method according to the invention are able to automatically adapt the medical data acquisition strategy/technique of the medical system. Optionally, after the adaptation of the medical data acquisition strategy/technique of the medical system took place, if the motion characteristic of the object does not exceed anymore the threshold, than the medical system and the method according to the invention are able to automatically retract the medical data acquisition strategy/technique.

In particular, the value of the thresholds stored in the threshold database might be estimated/calculated by means of the system for detecting and/or quantifying object motion, e.g. by means of the calculator, and notably from acquired object motion data and by using statistical analysis, or might be entered in the threshold database by an operator. Notably, the object motion data could be also obtained by statistical analysis of the medical image data. Each object motion threshold defines in particular an object motion characteristic, such as an amplitude, direction, or frequency, for a medical technique or imaging procedure used for acquiring the object motion data and to which it is specific, and that should not be exceeded during the acquisition of the medical data The object motion thresholds might be preferentially stored in a storage medium of the system for detecting and/or quantifying object motion like the threshold database. In particular, medical data acquired when an object motion has been detected are classified in the second set of data if the amplitude of the object motion has an absolute value that is greater than a determined or predefined threshold, and is classified in the first set of data otherwise. Preferentially, only object motion amplitudes falling outside a predetermined tolerance interval are detected by means of the object motion detection according to the invention, wherein the tolerance interval is defined as a set of motion amplitudes comprised between two thresholds according to the invention. In particular, the object motion threshold value is automatically determined from the object motion data and/or predefined (e.g. theoretically estimated) in function of the medical system and/or the method used for acquiring the medical data, and then preferentially stored in the threshold database. Preferentially, the (predefined) motion threshold depends on the medical technique used by the medical system during the medical examination of the object, and in particular, at least one motion threshold is predefined for each medical technique that might be used by the medical system. For instance, in the case of MRI, the motion threshold or predefined motion threshold depends on the imaging procedure used during the medical examination of the object as explained in detail later, and preferentially, at least one threshold is predefined for each imaging procedure that might be performed by the MRI system.

According to the invention, object motion might be detected contemporaneously with the acquisition of medical data, or by statistical or other analysis of the medical data during acquisition, and object motion amplitude calculated from object motion data acquired simultaneously to the acquisition of medical data, or deducted by comparison between object motion data acquired before starting the acquisition of medical data and object motion data acquired simultaneously to the acquisition of medical data. In particular, if, during medical data acquisition, the object motion amplitude remains within a predetermined tolerance interval, then the medical data are classified in the first set of data. In the case of medical imaging for in-stance, image quality is almost not affected by the object motion, or, if it is not the case, suitable techniques might be used to correct image artifacts. If the object motion amplitude exceeds a predetermined tolerance interval or a threshold, then the medical data have to be classified in the second set of data. Advantageously, according to the present invention, each threshold value and/or tolerance interval is defined specifically for the medical technique used by the medical system, and thus for a specific working configuration of the medical system when acquiring medical data.

Advantageously, the present invention gives a direct access to information about a current motion amplitude of the object at any time, letting thus possible at any point (immediately before or during the acquisition of medical data, e.g. before or during a medical scan) to assess whether the medical data are going to provide useful medical information or not, for example, to assess whether the image quality provided by a medical imaging system according to the present invention will be acceptable or not. If the motion amplitude of the object is qualified as "not tolerable," i.e. exceeds a determined or predefined threshold for a current acquisition method, subsequent measures can be taken.

Advantageously, the present invention allows to take account of the sensitivity of the medical system used for acquiring the medical data, since depending on the medical system and/or the method used for acquiring the medical data, different thresholds (i.e. different tolerable motion amplitudes) might be determined or pre-defined, wherein each threshold might be specific to the medical system and/or method used. In particular, the threshold might also be time dependent: different thresholds might be determined depending on when the object motion occurred during the medical data acquisition. For example, in the case of MRI, at least a first threshold might be defined for object motion happening during acquisition of centre k-space medical data, and at least a second threshold might be defined for object motion happening at high frequencies, i.e. during acquisition of k-space borders, assuming that motion artifacts in the k-space centre affect the final image quality much stronger than the same effects occurring at the k-space borders. In other words, the classification of the medical data in the two sets of data depends on the medical system and/or used method, as well as on the time.

For example, it is known that the sensitivity to object motion for Single-Shot-Method (in MRI, e.g. EPI or HASTE) or self-navigated method (e.g. BLADE in MRI) is low compared to the sensitivity to object motion for Multi-Shot-Method without navigation (e.g. TSE) (e.g. a motion amplitude equivalent to a shift of 0.5 pixel in the medical image of the object suffices for inducing image blur in standard acquisition methods without navigation, while Multi-Shot-Methods with navigation are able to effectually compensate sporadic object motion with moderate object motion amplitude). Unfortunately, the above-mentioned methods are not able to compensate permanent object motion and/or object motion amplitudes exceeding some threshold values. The present invention advantageously allows to adapt the classification of the medical data in each of the first and second sets of data in function of the medical technique used for imaging or examining the object. In other words, depending on the medical technique used for examining the object, medical data that is acquired during a certain object movement might be classified in the first set of data if the medical technique is little sensitive to object motion, or in the second set of data if the medical technique is very sensitive to object motion. Advantageously, the determination of the predetermined threshold and/or tolerance interval according to the invention is thus adapted to the medical technique used for making a diagnosis of the object.

According to the present invention and an optional embodiment, object motion data might be used before starting the medical data acquisition for automatically determining, for each medical technique of the medical system that might be used for the medical examination of the object, at least one threshold value or tolerance interval by means of the system for detecting and/or quantifying object motion, the threshold value or tolerance interval defining which object motion amplitude/frequency/direction is tolerable or not for the medical system when using the medical technique. In particular, the determination of the tolerance interval and/or threshold might be done automatically by processing the object motion data (by using e.g. statistical analysis of the object motion data) and/or manually by an operator by tuning the threshold value. Preferentially, the tolerance interval and/or threshold might be predetermined by means of theoretical calculations and saved in the threshold database of the medical system, wherein in particular at least one threshold and/or tolerance interval is predetermined for each medical technique that the medical system might use for acquiring the object motion data. Preferentially, the tolerance interval and/or threshold might be manually tuned by the operator during the medical examination from the predetermined tolerance interval and/or threshold value. For example, in function of the medical technique, respectively imaging procedure, used by the medical system, respectively used by the MRI system, for the acquisition of the object motion data, a tolerance interval and/or threshold is automatically chosen by the system for detecting and quantifying the motion of the object among the values of the tolerance interval/threshold saved in the threshold database. Typical object motion values used for determining the tolerance interval and/or threshold are for example the maximal displacement of the object or a part of the object within an acquisition volume (amplitude), and the frequency of occurrence of motion for the object or part of the object over a predetermined tolerance value (e.g. ½ pixel).

During the medical data acquisition, e.g. simultaneously to the acquisition of medical data and/or also between two series of medical data acquisition for the object, the object motion is in particular measured and determined, notably in real time, by means of the system for detecting and/or quantifying object motion. Preferentially, object motion data are thus continuously acquired during the medical data acquisition and compared to the threshold and/or tolerance interval for determining if an object motion is tolerable or not. The comparison between object motion data acquired during the medical data acquisition and the tolerance interval and/or threshold allows to directly determine, notably in real time, if medical data have to be classified in the first set or second set of data. The classification depends preferentially on the amplitude and frequency of an object motion. For example, a singular moderate displacement of the object might be tolerable (first set of data), while a continuous moderate displacement of the object might be classified as intolerable (second set of data).

According to a preferred embodiment, as soon as medical data are classified in the second set of data, i.e. as soon as an object motion overcomes a threshold or is not in the tolerance interval, the method according to the invention proposes to adapt the data acquisition strategy/technique. In particular, in addition to the examples of adaptation (1)-(4) previously given for medical imaging, the adaptation of the data acquisition strategy/technique of the medical system might comprise one of the following actions, which might be in particular automatically implemented:

(5) sending a visual and/or acoustic message to the operator of the medical system for indicating to the operator that a motion overcoming a threshold or falling beyond a tolerance interval occurred, and that a manual adaptation of the data acquisition strategy/technique has to take place. After sending such a visual and/or acoustic message to the operator, the medical system may automatically provide the operator with different choices of actions: e.g. the medical system may propose to the operator to stop the medical data acquisition (if it has not yet stopped automatically), so that the operator may provide some instructions to the patient (object), and then continue with the acquisition of medical data;

(6) sending a warning message to the operator of the medical system, wherein the warning message requests a reacquisition of medical data falling within the second set of data. In particular, an acknowledgement of the warning message by the operator automatically operates a reacquisition of the medical data falling within/comprised in the second set of data by means of the medical system. Advantageously, by this way, it is possible for the operator to calm down a patient before starting the reacquisition of medical data by acknowledging the warning message;

(7) sending to the operator a request for changing the medical data acquisition strategy, wherein the request for changing the medical data acquisition strategy/technique requests to interrupt the medical data acquisition and to choose a new strategy/technique for acquiring the medical data. Preferentially, at least one alternative strategy/technique is proposed to the operator according to the present invention. The alternative strategy/technique is preferentially an available strategy/technique of the medical system for acquiring medical data. In particular, acknowledgement by the operator of the request automatically operates a change of strategy/technique according to the alternative strategy/technique chosen by the operator. Advantageously, by this way, it is possible for the operator to calm down a patient before acknowledging the request;

(8) automatically providing an acoustic and/or visual message to the subject examined by the medical system, for instance automatically providing the examination volume with the acoustic and/or visual message. Advantageously, providing the examination volume with the acoustic and/or visual message makes it possible to inform the examined subject that he has to keep attention of possible motion of at least one part of his body. By this way, the cooperation of the patient is aroused. For example, acquisition of medical data belonging to the first set of data automatically turns on a blue light located in a position visible for the examined subject, for example in the examination volume of the medical system. The blue light is then preferentially maintained as long as medical data are classified in the second set of data. As soon as a medical data is classified in the second set of data, then the blue light is replaced by a red light indicating to the patient that he has to take care of possible body motions. Preferentially, the red light remains on as long as medical data continue to be classified in the second set during medical data acquisition, and is automatically switched off, and the blue light switched on, as soon as medical data are not anymore classified in the second set of data.

Preferably, the adaptation of the data acquisition strategy/technique by means of one of the actions (1)-(8) might be triggered by the acquisition of medical data belonging to the second set of data. In particular, as soon as a medical data is classified in the second set of data, then, at least one of the above-mentioned actions (1)-(8) is engaged. The engagement might be done with or without automatically interrupting the acquisition of medical data. Preferentially, at least one of the above-mentioned actions (1)-(8) is performed during the medical data acquisition and without stopping the medical data acquisition, i.e. while the medical data acquisition is running.

Preferably, if a medical data acquisition technique/strategy has been adapted, then, the adaptation might be maintained or used for the acquisition of further medical data for the same object, in particular until further acquired medical data are only classified in the first set of data. For example, if a medical data acquisition technique/strategy has been adapted by performing a manual adaptation ac-cording to step (5) or using a new medical data acquisition strategy/technique ac-cording to step (7), then the method according to the invention comprises maintaining the manual adaptation for step (5) or the new medical data acquisition strategy/technique for step (7). Preferentially, if the further medical data are only classified in the first set of data after the adaptation, then, the medical data acquisition technique/strategy as it is after the adaptation (i.e. the "adapted" medical data acquisition technique/strategy) might be replaced by the medical data acquisition technique/strategy as it was before the adaptation.

Preferably, the acquisition of object motion data takes place before starting the acquisition of medical data, for example in a dedicated measurement session for identifying a cooperation capacity of the object (e.g. patient) or in a dedicated measurement session for calibrating the medical system, and enables a determination of motion characteristics/parameters by means of the system for detecting and/or quantifying object motion. Object motion characteristics/parameters are for example the motion amplitude, direction, frequency, etc. In particular, the method according to the invention is able to define and to choose from the object motion characteristics/parameters at least one adaption of the data acquisition strategy/technique that will take place during the medical data acquisition if medical data are classified in the second set of data. In other words, the present invention proposes to determine from object motion characteristics/parameters and before the acquisition of medical data, which adaptation of the data acquisition strategy/technique will be the most suitable for the object.

Preferably, the method according to the invention comprises decreasing a threshold value if contrast means for enhancing a contrast between different parts of the object/patient are used, and consequently improving the acquisition of object motion data and the determination of the object motion characteristics/parameters. Indeed, in case of use of contrast means, then it is better that the acquisition method does not change (i.e. no adaptation takes place). For example, during a "pre-contrast scan" (i.e. a scan taking place before injecting a contrast means in a patient, by opposition to a "post-contrast scan") by means of a medical imaging system like an MRI system that takes place during the medical data acquisition, a more conservative threshold is used (i.e. the threshold is decreased so that already small object motions are detected). Consequently, the acquisition technique/strategy might be adapted during the pre-contrast scan. Then, during the examination/scan with contrast means, no adaptation should take place. For this purpose, the threshold according to the invention might be increased for the acquisition of medical data acquired when the object comprises a contrast mean (post-contrast scan), or any adaptation of the data acquisition strategy/technique might be prohibited by the medical system, or the medical system may inform the operator about an ongoing motion (and let him decide how to proceed) while continuing the scan.

Preferably, the object motion detection and/or the object motion quantification by means of the system for detecting and/or quantifying object motion might also take place between two medical data acquisition sessions, each session being Preferably separated by a time period during which no medical data are acquired and object motion data are acquired, allowing for example to further check and modify the object motion characteristics/parameters in case of relevant change in the object motion.

Preferably, the method according to the invention comprises providing a file comprising information, e.g. object motion data, related to object motions occurred during medical data acquisition, for example in the form of a quality index. By means of the file, it is advantageously possible to determine, for an operator, potential artifacts risks in medical images, or to identify "intolerable" medical images retroactively. Preferably, the information related to object motions may be automatically stored/saved in DICOM format, e.g. the file is characterized by a DICOM file format. Preferably, the file is a medical image. In other words, the method according to the invention comprises in particular providing a medical image in a DICOM format including information related to object motion, e.g. in the form of a quality index. Preferably, a DICOM entry is associated to medical images, for example in the form of an image comment, for which object motion occurred.

Finally, the present invention also claims the medical system for carrying out the previously described method for adapting a medical system to an object motion occurring during a medical examination of the object by means of the medical system. The claimed invention will be best understood from the following description of a specific embodiment when read in connection with the accompanying drawing:

Other features which are considered as characteristic for the invention are set forth in the appended claims.

Although the invention is illustrated and described herein as embodied in a method for adapting a medical system to patient motion occurring during medical examination and system therefor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The FIGURE of the drawing is as schematic representation of the method and system according to the invention.

DETAILED DESCRIPTION OF THE INVENTION

Referring now to the sole FIGURE of the drawing in detail there is shown a schematic of a medical system according to the invention. The medical system is a medical imaging system 2, e.g. an MRI system, designed for carrying out the previously described method. The medical imaging system 2 is capable of performing a medical examination of an object 1 in particular by imaging the object 1. The medical imaging system 2 is working according to a medical imaging technique. The medical imaging system 2 comprises a system 3 for detecting and quantifying a motion of the object 1 during an acquisition of medical data, wherein the system 3 for detecting and quantifying a motion of the object 1 is able to directly identify and qualify the occurrence of object motion and to automatically suggest an adaptation of the medical data acquisition strategy/technique to the object motion. The method carried out by the medical imaging system 2 is also described in FIG. 1. Indeed, the latter shows a schematic representation of the method for adapting the medical system to the object motion occurring during a medical examination of the object 1, e.g. a patient head, by means of the medical imaging system 2. The method comprises:

- placing, for example at a time t1, the object 1 to be imaged in an examination volume of the medical imaging system, the examination volume defining a position and place allowing the examination of the object 1 by the medical imaging system 2, for example in the tube of an MRI scanner;
- before starting an acquisition of medical data by means of the medical imaging system 2:
- starting at a time t2 an acquisition of object motion data M by means of the system 3 for detecting and/or quantifying object motion, wherein the object motion data are acquired when the object is in the examination volume of the medical imaging system 2;
- after a predetermined time t3−t2, stopping the acquisition of object motion data by means of the system 3 for detecting and/or quantifying object motion;
- starting, for example at a time t4, an acquisition of medical data D by means of the medical imaging system 2;
- during the acquisition of the medical data D:
- using the object motion data for automatically classifying medical data in two sets of data, respectively a first set of data for which object motion during medical data acquisition is tolerable, and a second set of data for which object motion during medical data acquisition is not tolerable;
- rejecting, preferably automatically rejecting, medical data belonging to the second set of data and adapting, preferentially automatically adapting, the medical data acquisition strategy/technique of the medical imaging system 2 in function of the object motion;
- preferably, acquiring further object motion data M' for updating the classification of medical data in the two sets of data, wherein the acquisition of the further object motion data M' might take place during a time interval t6−t5 comprised in the period of time t7−t4 dedicated to the acquisition of medical data D with t6−t5<t7−t4, and/or during a time interval t9−t8 separating the session of the acquisition of the medical data D from a session of a further acquisition of medical data D'. The acquisition of object motion data M1 might also take place during the whole time interval t11−t10 simultaneously to the acquisition of medical data D'.

In particular, the object motion data are analyzed and processed by the system 3 for detecting and/or quantifying object motion in order to detect and quantify the object motion simultaneously to the acquisition of medical data. Preferably, the system 3 for detecting and/or quantifying object motion is able to cooperate with the medical imaging system 2 in order to automatically suggest an adaptation of the medical data acquisition strategy/technique to the object motion by means of the medical imaging system 2, and/or to automatically proceed to the adaptation of the medical data acquisition strategy/technique by changing an acquisition parameter/method of the medical imaging system 2.

The invention claimed is:

1. A method for adapting a medical imaging system to an object motion occurring during a medical examination of the object by way of the medical imaging system, the method comprising:

placing the object to be examined in an examination volume of the medical imaging system;

starting an acquisition of medical data by way of the medical imaging system, and during the acquisition of the medical data:

in the medical imaging system, using object motion data for classifying the medical data in two sets of data, respectively a first set of data for which object motion during medical data acquisition is tolerable, and a second set of data for which object motion during medical data acquisition is not tolerable, the object motion data being information related to the motion of the object while the object is present in the examination volume of the medical imaging system, in the medical imaging system, in response to determining that the object motion during the medical data acquisition is not tolerable, rejecting the medical data belonging to the second set of data by withdrawing the rejected medical data from being medically data processed before using any of the medical data for reconstructing a medical image of the object, and reducing a sensitivity of the medical imaging system to motion of the object as a result of adapting the medical data acquisition strategy/technique of the medical imaging system by automatically selecting a medical data acquisition strategy/technique from a plurality of available medical data acquisition strategies/techniques as a function of the object motion and the object motion thresholds defined for each of the plurality of available medical data acquisition strategies/techniques; and in the medical imaging system, determining different object motion thresholds for each medical technique that can be used by the medical imaging system, wherein each object motion threshold is configured for ruling the classification of the medical data into the two sets of data, wherein each of the object motion thresholds defines an object motion amplitude that is not to be exceeded by the movement of the object during the acquisition of the medical data, wherein each of the object motion thresholds is specifically determined for each medical technique that is used for examining the object, and wherein the medical imaging system automatically selects a medical data acquisition strategy/technique from the plurality of available medical data acquisition strategies/techniques as a function of the object motion and the object motion thresholds defined for each of the plurality of available medical data acquisition strategies/techniques;

wherein the plurality of available medical data acquisition strategies/techniques comprise medical imaging techniques including echo planar imaging (EPI), turbo spin echo (TSE), single/multi-shot, and navigated;

wherein the plurality of available medical data acquisition strategies/techniques comprise medical protocols including matrix size and field of view (FOV); and wherein a threshold database stores, for each of the medical imaging techniques and for each of the medical protocols, a threshold value that defines a maximum tolerable motion characteristic for the object.

2. The method according to claim 1, which comprises acquiring the object motion data by way of the medical imaging system, wherein the object motion data are acquired when the object is in the examination volume.

3. The method according to claim 2, which comprises performing the step of acquiring object motion data by way of the medical imaging system before starting the acquisition of medical data or in parallel to the acquisition of medical data.

4. The method according to claim 1, wherein the step of adapting the medical data acquisition strategy/technique comprises changing the acquisition method and/or changing the measurement parameters of the medical imaging system.

5. The method according to claim 1, comprising detecting and quantifying the object motion during medical data acquisition.

6. The method according to claim 1, wherein medical data acquired when an object motion has been detected are classified in the second set of data if the amplitude of the object motion has an absolute value that is greater than the threshold from the medical technique, and the medical data are otherwise classified in the first set of data.

7. The method according to claim 1, which comprises acquiring further object motion data for optimizing the classification of medical data in the two sets of data.

8. The method according to claim 1, wherein the medical imaging system includes at least one device selected from the group consisting of:
  a camera system;
  a pulse measurement system;
  a breathing belt; and
  an ECG system.

9. The method according to claim 1, which comprises detecting object motion simultaneously with acquiring medical data, and calculating an object motion amplitude from object motion data acquired simultaneously with the acquisition of medical data or deducted by comparison between object motion data acquired before starting the acquisition of medical data and object motion data acquired simultaneously with the acquisition of medical data.

10. The method according to claim 1, wherein the step of adapting the data acquisition strategy/technique comprises one of the following actions:
  a) sending a visual and/or acoustic message to an operator of the medical imaging system for indicating to the operator that a motion overcoming a threshold or falling beyond a tolerance interval occurred;
  b) sending a warning message to the operator of the medical imaging system, wherein the warning message requests a reacquisition of medical data falling within the second set of data;
  c) sending to the operator a request for changing the medical data acquisition strategy, wherein said request for changing the medical data acquisition strategy/technique requests to interrupt the medical data acquisition and to choose a new strategy/technique for acquiring the medical data;
  d) automatically providing the examination volume with an acoustic and/or visual message.

11. The method according to claim 1, which comprises providing a medical image of the object in a DICOM format including information related to the object motion.

12. The method according to claim 1, which comprises:
  during the acquisition of the medical data by the medical imaging system, identifying and qualifying an occurrence of object motion, and in response to determining that the object motion during the medical data acquisition is not tolerable, rejecting medical data belonging to the second set of data by withdrawing the rejected medical data from being medically data processed before using any of the medical data for reconstructing a medical image of the object; and
  during the acquisition of the medical data by the medical imaging system, said adaptation of the medical data acquisition strategy/technique in dependence on the object motion is performed in response to an automatically-made suggestion for the adaptation.

13. The method according to claim 12, which comprises automatically proceeding to the adaptation of the medical data acquisition strategy/technique.

14. The method according to claim 1, wherein the plurality of available medical data acquisition strategies/techniques include: a single-shot imaging technique and a multi-shot technique.

* * * * *